(12) United States Patent
Lau et al.

(10) Patent No.: US 11,572,561 B2
(45) Date of Patent: Feb. 7, 2023

(54) METHOD AND COMPOSITION FOR INHIBITING GROWTH OF BACTERIUM

(71) Applicant: City University of Hong Kong, Kowloon (HK)

(72) Inventors: Chi Kong Terrence Lau, Kowloon (HK); Oi Kwan Law, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 16/906,019

(22) Filed: Jun. 19, 2020

(65) Prior Publication Data
US 2021/0395731 A1   Dec. 23, 2021

(51) Int. Cl.
| | | |
|---|---|---|
| *A61K 39/108* | (2006.01) | |
| *A61K 39/00* | (2006.01) | |
| *A61K 39/38* | (2006.01) | |
| *C12N 15/113* | (2010.01) | |
| *A61K 31/7088* | (2006.01) | |
| *A61K 31/43* | (2006.01) | |
| *A61K 31/546* | (2006.01) | |
| *A61K 31/165* | (2006.01) | |
| *A61K 31/65* | (2006.01) | |
| *A61K 31/7048* | (2006.01) | |
| *A61K 31/7056* | (2006.01) | |
| *A61K 31/496* | (2006.01) | |
| *A61K 31/5383* | (2006.01) | |
| *A61K 31/4709* | (2006.01) | |
| *A61K 31/5377* | (2006.01) | |
| *C12N 7/00* | (2006.01) | |
| *A61K 9/51* | (2006.01) | |
| *A61P 31/04* | (2006.01) | |

(52) U.S. Cl.
CPC .............. *C12N 15/113* (2013.01); *A61K 9/51* (2013.01); *A61K 31/165* (2013.01); *A61K 31/43* (2013.01); *A61K 31/4709* (2013.01); *A61K 31/496* (2013.01); *A61K 31/5377* (2013.01); *A61K 31/5383* (2013.01); *A61K 31/546* (2013.01); *A61K 31/65* (2013.01); *A61K 31/7048* (2013.01); *A61K 31/7056* (2013.01); *A61K 31/7088* (2013.01); *A61P 31/04* (2018.01); *C12N 7/00* (2013.01); *C12N 2310/14* (2013.01); *C12N 2320/31* (2013.01); *C12N 2795/00043* (2013.01)

(58) Field of Classification Search
CPC .................................................. C12N 15/113
See application file for complete search history.

(56) References Cited

U.S. PATENT DOCUMENTS

| 2007/0020624 A1 * | 1/2007 | Rubenfield ............ C07K 14/21 |
| | | 435/6.15 |
| 2018/0265913 A1 * | 9/2018 | Keller .................... C12Q 1/689 |

OTHER PUBLICATIONS

Qureshi, Medscape, https://emedicine.medscape.com/article/226748-medication#:~:text=Pseudomonas%20infection%20can%20be%20treated,in%20conjunction%20with%20an%20aminoglycoside;Mar. 3, 2020. (Year: 2020).*
Hoppner, Horm Re. 2002, 58 Suppl. 3:7-15 (Year: 2002).*

\* cited by examiner

*Primary Examiner* — Brian Gangle
*Assistant Examiner* — Lakia J Jackson-Tongue
(74) *Attorney, Agent, or Firm* — Renner Kenner Greive Bobak Taylor & Weber

(57) ABSTRACT

A method of inhibiting growth of a bacterium including steps of: a) delivering a polynucleotide including a sequence of SEQ ID NO: 1 or a homologue thereof to the bacterium, and b) contacting the bacterium with an effective amount of an antibiotic; wherein the bacterium is *Pseudomonas aeruginosa*. A method of treating a subject suffering from an infection caused by a bacterium which is *Pseudomonas aeruginosa* and the method including steps of: i) delivering said polynucleotide to a tissue infected by the bacterium or a bacterial cell in the subject; and ii) administering an effective amount of an antibiotic to the subject. A composition and a recombinant plasmid containing said polynucleotide.

11 Claims, 12 Drawing Sheets

Specification includes a Sequence Listing.

Figure 1

SEQUENCE LISTING

<160> NUMBER OF SEQ ID NOS: 6

<210> SEQ ID NO 1
<211> LENGTH: 106
<212> TYPE: DNA
<213> ORGANISM: Pseudomonas aeruginosa

<400> SEQUENCE: 1
gcggttgcgc ggccaggcac tggtcgagga gatgcaccag ggtggcctgt tccaccgggg      60
tgagcggggc aaacaactcg tcatgcacgc gtgacatgat ggcctc                    106

<210> SEQ ID NO 2
<211> LENGTH: 128
<212> TYPE: DNA
<213> ORGANISM: Pseudomonas aeruginosa

<400> SEQUENCE: 2
gaatgttctt aaatatcctc aagcggttgc gcggccaggc actggtcgag gagatgcacc      60
agggtggcct gttccaccgg ggtgagcggg gcaaacaact cgtcatgcac gcgtgacatg     120
atggcctc                                                             128

```
<210> SEQ ID NO 3
<211> LENGTH: 59
<212> TYPE: DNA
<213> ORGANISM: Pseudomonas aeruginosa

<400> SEQUENCE: 3
gctgtacatc cctggatcct ttcccggcct gctccacgcg gccgggattt tttttgccc        59

<210> SEQ ID NO 4
<211> LENGTH: 129
<212> TYPE: DNA
<213> ORGANISM: Pseudomonas aeruginosa

<400> SEQUENCE: 4
gcgaacccca agggtatttc ccgaccagct cccccgcggt cgggattttt ttttgcctgt        60
cgctcagcgc ttcgggtcga agggcgaata gccccgccgg cgcaggctcg ccaggggcgc       120
gaacagcgg                                                               129

<210> SEQ ID NO 5
<211> LENGTH: 32
<212> TYPE: DNA
<213> ORGANISM: Artificial Sequence
<220> FEATURE:
<223> OTHER INFORMATION: Synthesized

<400> SEQUENCE: 5
cgactgcaga gatttcagtg caatttatct ct                                      32

<210> SEQ ID NO 6
<211> LENGTH: 32
<212> TYPE: DNA
<213> ORGANISM: Artificial Sequence
<220> FEATURE:
<223> OTHER INFORMATION: Synthesized

<400> SEQUENCE: 6
gatctgcagt tcacagttct ccgcaagaat tg                                      32
```

METHOD AND COMPOSITION FOR INHIBITING GROWTH OF BACTERIUM

SEQUENCE LISTING

The Sequence Listing file entitled "sequencelisting" having a size of 8,192 bytes and a creation date of Jun. 19, 2020, that was filed with the patent application is incorporated herein by reference in its entirety

TECHNICAL FIELD

The present invention relates to a polynucleotide particularly a RNA molecule for inhibiting the growth of a bacterium, and a composition containing said polynucleotide. The invention also relates to a method of inhibiting the growth of a bacterium or inhibiting a bacterial infection by applying said polynucleotide.

BACKGROUND OF THE INVENTION

Bacteria with multiple drug resistance (or multidrug resistance, MDR) have become a global issue worldwide, and hundreds of thousands of people's lives are threatened every year. In recent years, a steady increase in the MDR of *Pseudomonas aeruginosa* (*P. aeruginosa*) has been reported. *P. aeruginosa* is a gram-negative bacterium of the family Pseudomonadaceae, and it can switch from being an environmental isolate (soil and water) to a human pathogen.

*P. aeruginosa* causes nosocomial pneumonia, catheter and urinary tract infections, sepsis in burn wound and immunocompromised patients, as well as chronic pulmonary inflammation in cystic fibrosis patients. One of the major characteristics of this bacterium is its resistance to antibiotics, which is due to the highly coordinated and complex transcriptional regulatory networks it possesses, resulting in the assimilation of signals originating from a multitude of different environments, such as the expression of different sets of genes to facilitate growth in drug-induced stress environments. The emerging MDR strains were resistant to fluoroquinolones, cephalosporins, carbapenems, and aminoglycosides. Thus, the choice for clinical treatment of *P. aeruginosa* infection is very limited.

Accordingly, there remains a need for developing compounds or methods that can be used against bacteria particular *P. aeruginosa* which have multidrug resistance.

SUMMARY OF THE INVENTION

In one aspect, there is provided a method of inhibiting growth of a bacterium comprising steps of:
 a) delivering a polynucleotide comprising a sequence of SEQ ID NO: 1 or a homologue thereof to the bacterium, and
 b) contacting the bacterium with an effective amount of an antibiotic;
 wherein the bacterium is *Pseudomonas aeruginosa*.

In another aspect, there is provided a method of treating a subject suffering from an infection caused by a bacterium, the bacterium is *Pseudomonas aeruginosa* and the method comprising steps of:
 i) delivering a polynucleotide comprising a sequence of SEQ ID NO: 1 or a homologue thereof to a tissue infected by the bacterium or a bacterial cell in the subject; and
 ii) administering an effective amount of an antibiotic to the subject.

In a still further aspect, there is provided a recombinant plasmid containing a polynucleotide comprising a sequence of SEQ ID NO: 1 or a homologue thereof.

In another aspect, there is provided a composition comprising a polynucleotide comprising a sequence of SEQ ID NO: 1 or a homologue thereof.

The inventors through experiments identified various RNA sequences that were downregulated in the MDR clinical isolates of *P. aeruginosa*, and the inventors demonstrated that overexpression of a particular RNA sequence, SEQ ID NO: 2 (denoted as AS1974), was able to transform the MDR clinical strain to a drug sensitive strain. It was found that SEQ ID NO: 2 is an important regulator to moderate the expression of several drug resistance pathways, including membrane transporters and bio film-associated antibiotic-resistant genes, and its expression is regulated by the methylation sites located at the 5' UTR of the gene. It was also found that the bacterial cell transformed with a recombinant vector containing SEQ ID NO: 2 has an improved sensitive towards antibiotics and was more susceptible to the antibiotics compared to the strain without transformation. Accordingly, the identified polynucleotide of the present invention is suitable for developing into clinical applications or for research purposes. The present invention at least provides an alternative approach for inhibiting the growth of a bacterium which may be present in a host.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 1 is a table showing the MIC of six clinical isolates and the sRNA-transformed strains which were measured using microbroth method.

DETAILED DESCRIPTION OF THE EMBODIMENTS

Figure 2A:
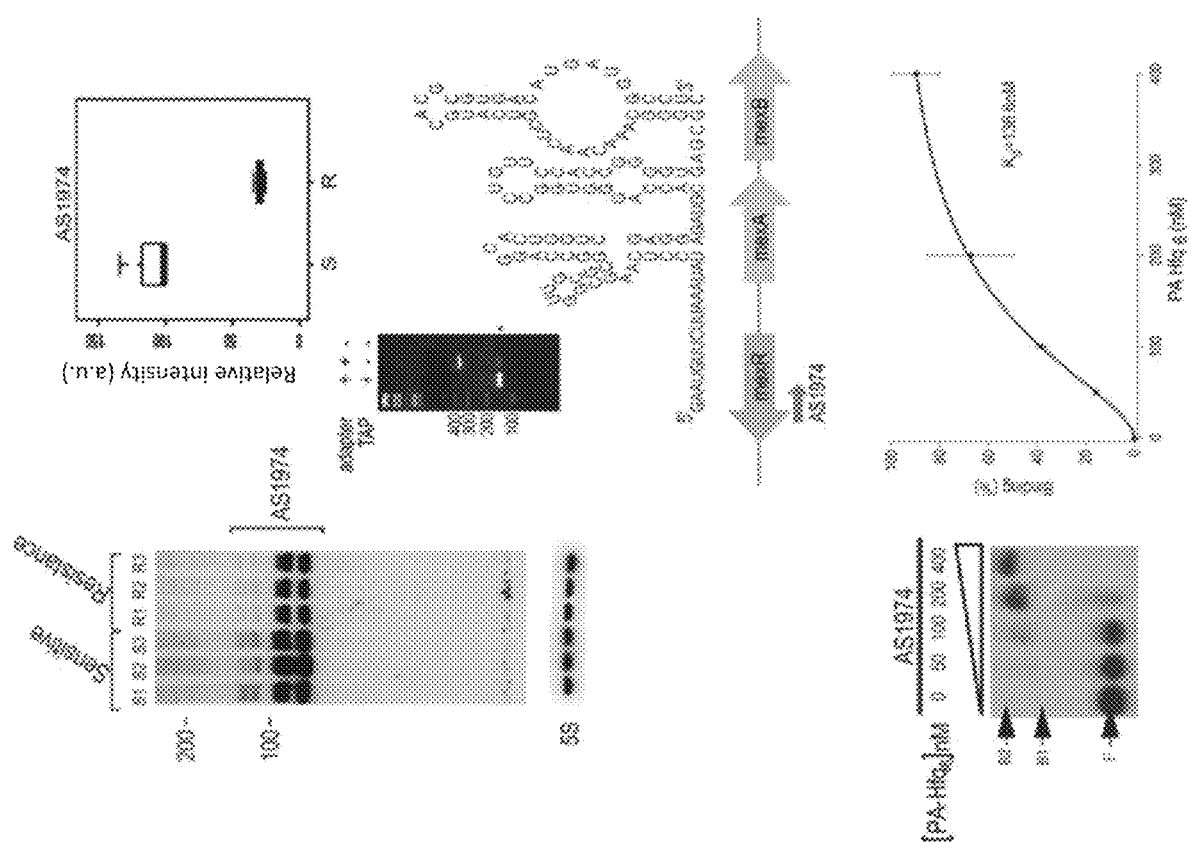
FIG. 2A shows the Northern blot analysis of 50 RACE, secondary structure prediction, and electrophoretic mobility shift assay (EMSA) of a sRNA AS1974 which has a sequence of SEQ ID NO: 2.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a," "an," and "the," are intended to include the singular and plural forms unless the context clearly indicates otherwise.

The present invention in an aspect provides a polynucleotide for inhibiting the growth of a bacterium particularly a gram-negative bacterium having a multidrug resistance. Preferably, the bacterium is P. aeruginosa including P. aeruginosa having a drug resistance against one or more conventional antimicrobial agents. For example, P. aeruginosa has a drug resistance against at least two conventional antibiotics including, but are not limited to, an aminoglycoside antibiotic, a cephalosporin antibiotic, a beta-lactam antibiotic, and a fluoroquinolone antibiotic.

In an embodiment, the bacterium or a strain thereof may have a decreased expression in AS1974 (SEQ ID NO: 2), IGR2780 (SEQ ID NO: 3) and/or AS2779 (SEQ ID NO: 4) RNA, resulting in a multidrug-resistant phenotype. IGR2780 is located at the intergenic region between PA2770 and PA2771. AS1974 and AS2779 are located at the antisense region of mexR and PA2769, respectively. The inventors through Northern blot analysis found that these RNAs, particularly sRNAs, were substantially downregulated in all drug-resistant strains compared with all drug-susceptible strains. The inventors thereby identified and developed a polynucleotide that can help inducing the sensitivity of a multidrug-resistant bacterium towards an antimicrobial agent for treatment or preventive measures.

The polynucleotide of the present invention is capable of suppressing the expression of a membrane protein including mexD, chtA and prc proteins, a transporter gene including major facilitator superfamily, a flagella gene including pilD, and a gene in relation of antibiotic resistance including ndvB gene. It may thereby induce the expression of a regulating gene to control or restrict the resistance against an antibiotic. The polynucleotide is also capable of inducing the sensitivity of a bacterium towards an antimicrobial agent.

The polynucleotide may be a RNA which may be single or double-stranded. In a particular embodiment, the polynucleotide is provided in the form of a sRNA molecule for insertion into a vector for subsequent delivery or transformation of a target bacterial cell or strain. In an embodiment, the polynucleotide of the invention may be encapsulated in a bacteriophage or a nanoparticle to be delivered to a bacterium or a strain thereof.

Preferably, the polynucleotide of the present invention comprises or consists of a sequence of SEQ ID NO: 1 or a homologue thereof. In an embodiment, the polynucleotide comprises or consists of a sequence of SEQ ID NO: 2 or a homologue thereof. The term "homologue" used herein refers to a polynucleotide having a sequence identity of at least 70%, at least 80%, at least 90%, at least 95% or at least 99% to the polynucleotide according to the present invention. In an embodiment, the homologue of the polynucleotide has at least 90%, 91%, 92%, 93%, 94%, 95%, 96%, 97%, 98%, or 99% overall sequence identity to SEQ ID NO: 1 or 2. In a particular embodiment, the polynucleotide consists of a sequence of SEQ ID NO:2 or a homologue thereof.

The inventors found that the polynucleotide of the present invention particularly the polynucleotide having a sequence of SEQ ID NO: 2 is useful to transform a bacterial strain thereby increasing its sensitivity towards an antimicrobial agent. It would be appreciated that the person skilled in the art is aware of suitable methods to incorporate the polynucleotide as described herein into a vector or a carrier including, but not limited to, a bacteriophage or a nanoparticle.

The polynucleotide is preferably used in combination with an antimicrobial agent. The antimicrobial agent may be commercially available or obtained via laboratory synthesis. The antimicrobial agent may be any agent that is currently available for therapy including antibiotics therapy. Preferably, the polynucleotide is used in combination with an antibiotic including an antibiotic that is capable of inhibiting the growth of a bacterium particularly a gram-negative bacterium or a gram-negative bacterium having a multidrug resistance.

In an embodiment, the antibiotic may be selected from the group consisting of an aminoglycoside antibiotic, a cephalosporin antibiotic, a beta-lactam antibiotic, a fluoroquinolone antibiotic, or a combination thereof. For example, aminoglycoside antibiotics include, but are not limited to, amikacin, tobramycin, and gentamicin; cephalosporin antibiotics include, but are not limited to, cefitbuten, cefpodoxime, cefotaxime, cefepime, cefamandole, cefatazidime, ceftriaxone, cefuroxime, cefotaxime, and cefoperazone; beta-lactam antibiotics include, but are not limited to, clavulanic acid (clavulanic acid may be used in combination with a cephalosporin—cefotaxime), sulbactam (sulbactam may be used in combination with a cephalosporin—cefoperazone (CFP)), imipenem, sultamicillin, ampicillin, meropenem, ertapenem, and tazobactam (tazobactam may be used in combination with an extended spectrum penicillin antibiotic—piperacillin); fluoroquinolone antibiotics include, but are not limited to, moxifloxacin, sparfloxacin, levofloxacin, ciprofloxacin, pefloxacin, norfloxacin, fleroxacin, and nalidixic acid; and other antibiotics include, but are not limited to piperacillin, trimethoprim, tigecycline, chloramphenicol.

In another embodiment, the antibiotic may be selected from the group consisting of amikacin, gentamicin, tobramycin, ceftibuten, cefepime, ceftazidime, cefriaxone, ceforaxmine, cefoperazone, sulbactam, imipenem, meropenem, ertapenem, peperacillin, tazobactam, moxifloxacin, pefloxacin, norfloxacin, fleroxacin, tigecycline, chloramphenicol, or a combination thereof.

The present invention also pertains to a composition particularly a pharmaceutical composition comprising the polynucleotide as described above as well as an antibiotic for inhibiting the growth of a bacterium. The composition may also be useful in treating, preventing or delaying progression of a bacterial infection in a subject. In an embodiment, the composition includes a polynucleotide comprising or consisting of a sequence of SEQ ID NO: 1 or a homologue thereof, or a sequence of SEQ ID NO: 2 or a homologue thereof. The polynucleotide may be provided in a vector or a carrier, or encapsulated in a bacteriophage or a nanoparticle.

The composition may include one or more antibiotics as described above. In particular, the composition may include at least one antibiotic selected from the group consisting of amikacin, gentamicin, tobramycin, ceftibuten, cefepime, ceftazidime, cefriaxone, ceforaxmine, cefoperazone, sulbactam, imipenem, meropenem, ertapenem, peperacillin, tazobactam, moxifloxacin, pefloxacin, norfloxacin, fleroxacin, tigecycline, chloramphenicol, or a combination thereof.

The composition may further include a suitable pharmaceutically tolerable excipient depending on the form of the composition. The pharmaceutically tolerable excipient may be one or more of a diluent, a filler, a binder, a disintegrant, a lubricant, a coloring agent, a surfactant, a gene delivery carrier and a preservative. The composition can be present in solid, semisolid or liquid form, preferably in liquid form. The composition may comprise further effective agents. The skilled person is able to select suitable pharmaceutically tolerable excipients depending on the form of the composition and is aware of methods for manufacturing compositions as well as able to select a suitable method for preparing the composition depending on the kind of pharmaceutically tolerable excipients and the form of the composition.

In an embodiment, the composition may further comprise a polynucleotide stabilizer. The polynucleotide stabilizer refers to any chemicals that are capable of maintaining the stability of the polynucleotide in the composition to minimize or avoid degradation, in particular those having ability to deactivate activity of nucleases or the like degrading the RNA molecules.

In one aspect, the invention also provides a recombinant plasmid containing a polynucleotide as described above, particularly a polynucleotide comprising a SEQ ID NO: 1 or a homologue thereof. In an embodiment, the polynucleotide comprising a sequence of SEQ ID NO: 2 or a homologue thereof.

In another aspect, the present invention pertains to a method of inhibiting the growth of a bacterium, in which the bacterium is as described above. The method comprises the steps of:
a) delivering a polynucleotide as described above to the bacterium, particularly the polynucleotide comprises or consists of a sequence of SEQ ID NO: 1 or a homologue thereof, and
b) contacting the bacterium with an effective amount of at least one antibiotic.

In an embodiment, the bacterium is a gram-negative bacterium and preferably is *P. aeruginosa*. The bacterium may have a resistance against one or more antibiotics particularly at least two conventional antibiotics before being treated or introduced with the polynucleotide in step a).

In step a), the polynucleotide may be provided in a vector or a carrier, or encapsulated in a bacteriophage or a nanoparticle to be delivered to the bacterium. In an embodiment, the polynucleotide comprising or consisting of a sequence of SEQ ID NO: 1, SEQ ID NO: 2 or a homologue thereof is inserted into a vector.

In an embodiment where the bacterium is incubated in a culture medium, the polynucleotide may be inserted to a vector for example a modified pMMB66EH vector that is engineered for RNA expression for transformation into the bacterium. In particular, the transformation may be conducted under a condition of 25 microfarad, 2.5 kV and 200Ω. The transformed cells can be recovered at 37° C. and with tetracycline at a suitable concentration and incubated at 37° C. overnight. A person skilled in the art would appreciate suitable conditions for transformation and incubation.

In an embodiment where the bacterium is present in a subject in particular a living organism such as an animal or a human, the polynucleotide may be encapsulated in the form of a bacteriophage for phage therapy (viral-mediated therapy) or encapsulated in a particle such as a nanoparticle for target therapy. The encapsulated polynucleotide may be delivered to a particular tissue and thereby in contact with the bacterium or bacteria for action. Step a) is advantageous in that the bacterium is transformed with the polynucleotide of the present invention, thereby regaining sensitivity towards one or more antibiotics. This allows conversion of a drug-resistant bacterium to a drug-sensitive bacterium. The bacterium can then be effectively suppressed or even killed by the aid of antibiotic applied in step b).

Step b) of the method may be performed simultaneously or after step a). In an embodiment, step b) is performed after step a) particularly after the polynucleotide is successfully delivered to the bacterium. An effective amount of an antibiotic as described above is provided to be in contact with the bacterium so as to inhibit the growth and/or suppress the proliferation of the bacterium.

It would be appreciated that the polynucleotide applied in step a) may be provided in the form of a composition as described above. The composition may include further agent that can improve the antibacterial effect achieved by performing the method as described herein.

The present invention also pertains to a method of treating a subject suffering from a bacterial infection caused by *Pseudomonas aeruginosa*. The method includes steps of i) delivering the polynucleotide as described above to the subject, particularly the polynucleotide is delivered to the tissue infected by the bacterium or a bacterial cell in the subject; and ii) administering an effective amount of an antibiotic as described above to the subject.

The polynucleotide is as described above and may be encapsulated in a bacteriophage or a nanoparticle to facilitate proper delivery.

The term "subject" used herein refers to a living organism and can include but is not limited to a human and an animal. The subject is preferably a mammal, preferably a human. The polynucleotide may be delivered through injection to the subject, preferably a human. The term injection encompasses intravenous, intramuscular, subcutaneous and intradermal administration.

Preferably, the target site for action is a bacterial infected tissue encompassing *P. aeruginosa* which has a drug resistance against one or more conventional antibiotics as described above. For instance, the polynucleotide may be delivered to the subject or tissue via transfection, electroporation or viral-mediated delivery. This is advantageous in that the polynucleotide can be directly delivered to the bacterial cells before any cellular degradation such as first pass metabolism. The polynucleotide may then modulate the expression of a membrane protein including mexD, chtA and prc proteins, a transporter gene including major facilitator superfamily, a flagella gene including pilD, and a gene in relation of antibiotic resistance including ndvB gene in the bacterial cell. Accordingly, the bacterial cell may be modulated to have an improved sensitivity towards an antibiotic particularly a convention antibiotic which the bacterium is resistant before delivery of the polynucleotide.

In step ii), an effective amount of an antibiotic is administered to the subject. The expression "effective amount" generally denotes an amount sufficient to produce therapeutically desirable results, wherein the exact nature of the result varies depending on the specific condition which is treated. In this invention, bacterial infection particularly *P. aeruginosa* infection is the condition to be treated and therefore the result is usually an inhibition or suppression of the growth or proliferation of bacterial cells, a reduction of bacterial cells or the amelioration of symptoms related to the infection including mild or severe inflammation as well as the associated complications.

The effective amount of the antibiotics used in the present invention may depend on the species, body weight, age and individual conditions of the subject. There are also standard dosages for conventional antibiotics. A person skilled in the art is able to determine the amount based on the condition of the subject. The antibiotic may be provided in solid, semi-solid or liquid form depending on the administration route. The antibiotic may be provided in the form of tablets, liquid, or pills.

In an embodiment, the antibiotic may be selected from the group consisting of an aminoglycoside antibiotic, a cephalosporin antibiotic, a beta-lactam antibiotic, a fluoroquinolone antibiotic, or a combination thereof. For example, aminoglycoside antibiotics include, but are not limited to, amikacin, tobramycin, and gentamicin; cephalosporin antibiotics include, but are not limited to, cefitbuten, cefpodoxime, cefotaxime, cefepime, cefamandole, cefatazidime, ceftriaxone, cefuroxime, cefotaxime, and cefoperazone; beta-lactam antibiotics include, but are not limited to, clavulanic acid (clavulanic acid may be used in combination with a cephalosporin—cefotaxime), sulbactam (sulbactam may be used in combination with a cephalosporin—cefoperazone (CFP)), imipenem, sultamicillin, ampicillin, meropenem, ertapenem, and tazobactam (tazobactam may be used in combination with an extended spectrum penicillin antibiotic—piperacillin); fluoroquinolone antibiotics include, but are not limited to, moxifloxacin, sparfloxacin, levofloxacin, ciprofloxacin, pefloxacin, norfloxacin, fleroxacin, and nalidixic acid; and other antibiotics include, but are not limited to piperacillin, trimethoprim, tigecycline, chloramphenicol.

In a particular embodiment, the antibiotic may be selected from the group consisting of amikacin, gentamicin, tobramycin, ceftibuten, cefepime, ceftazidime, cefriaxone, ceforaxmine, cefoperazone, sulbactam, imipenem, meropenem, ertapenem, peperacillin, tazobactam, moxifloxacin, pefloxacin, norfloxacin, fleroxacin, tigecycline, chloramphenicol, or a combination thereof.

Still further, the present invention pertains to a polynucleotide as described above for treating a bacterial infection or for inhibiting the bacterial infection. The bacterial infection is particularly *P. aeruginosa* infection. The invention also pertains to use of said polynucleotide in the preparation of a medicament for treating a bacterial infection. It would also be appreciated that the polynucleotide of the present invention can be used as a small RNA molecule to interfere the expression of certain genes in the target bacterial cells, thereby inhibiting the growth and proliferation of the target bacterium.

Accordingly, the present invention provides a novel and effective approach for improving the efficacy of a conventional antibiotic in treating a multidrug-resistant bacterial infection. This is advantageous in that the conventional antibiotics available on the market can continue to achieve their therapeutic effect against bacterial infections.

The examples set out below further illustrate the present invention. The preferred embodiments described above as well as examples given below represent preferred or exemplary embodiments and a skilled person will understand that the reference to those embodiments or examples is not intended to be limiting.

EXAMPLE

The inventors conducted experiments to compare the sRNA repertoires of three MDR clinical isolates and three drug susceptibility strains, and identified three specific sRNAs that were downregulated in MDR strains. One of the sRNAs, AS1974 having a sequence of SEQ ID NO: 2, was found to play significant roles in regulating various drug resistance pathways in *P. aeruginosa* and is able to transform the bacteria from drug-resistant to drug-sensitive.

Characterization of MDR Strains of Clinical Isolates

Figure 1:
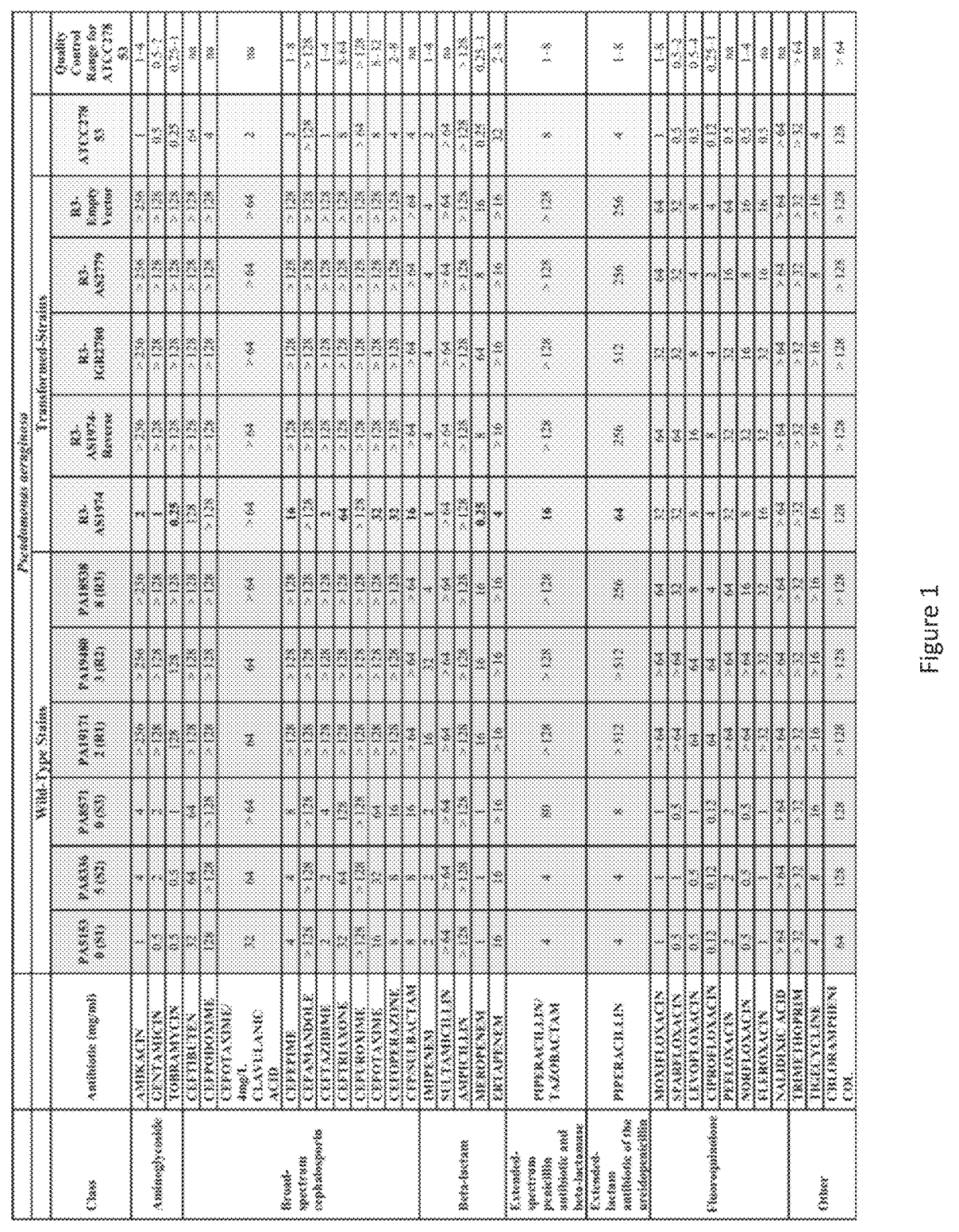

Six representative strains from clinical isolates, including 3 drug susceptible and 3 MDR of *P. aeruginosa*, were selected and cultured for further characterization. To define the susceptibility and resistance groups to different antibiotics, minimal inhibition concentration (MIC) assay was performed. ATCC 27853 was used as a reference to test the antimicrobial activity and susceptibility, with well-defined MIC values representative of susceptible, intermediate, and resistant phenol types, and also as a quality control test of antibiotic media. The criteria to define and distinguish between drug-susceptible and drug-resistant groups depend on the total number of drugs they resist among different classes of antibiotics, such as quinolone, aminoglycoside, cephalosporin, and penicillin. The resistance strains are defined as the strains that resist most of the drugs in the MIC assay, see FIG. 1.

FIG. 1 shows the MIC of six clinical isolates and the sRNA-transformed strains which were measured using microbroth method. Different classes of antibiotics including aminoglycoside, cephalosporin, beta-lactam, extended-spectrum penicillin beta-lactam, fluoroquinolone were used. Antibiotics susceptibility and resistance strains are highlighted. R3-AS1974, R3-AS2779 and R3-IGR2780 represent R3 strains transformed with the corresponding sRNA while R3-AS1974-Reverse represents R3 strains transformed the sRNA which sequence was reverse and complementary to AS1974 (negative control). R3-empty vector was used as vector control. The strain ATCC27853 was used for quality control.

Identification of MDR-Specific sRNAs in *P. aeruginosa*

In vitro RNA immunoprecipitation was performed by using recombinant Hfq followed by sRNA sequencing for all six strains. The sequencing libraries were constructed using the enriched sRNAs from different strains, and the sequencing was performed using Ion Torrent PGM sequencer, according to the protocol supplied by the company (Life Technologies). For each sample, more than 400,000 reads were mapped to the reference genome PAO1, and most of the reads were located at either coding regions or intergenic regions.

To identify the sRNAs that are specific to MDR, sRNAs that expressed with the fold change in log 2 scale>1 and q value % 0.05 between drug-susceptible or drug-resistant strains were selected. Three sRNAs, including IGR2780, AS1974, and AS2779 (FIG. 2A to FIG. 2C) were identified. IGR2780 is located at the intergenic region between PA2770 and PA2771. AS1974 and AS2779 are located at the antisense region of mexR and PA2769, respectively. As shown in the northern blot analysis of FIG. 2A to 2C, three sRNAs were downregulated in all drug-resistant strains compared with all drug-susceptible strains.

To further characterize these sRNAs, the transcription start site (TSS) and the promoters of each sRNA were identified using rapid amplification of cDNA ends (RACE) analysis. Intriguingly, both AS1974 and AS2779 possessed two TSSs and thus different isoforms, whereas IGR2780 had only one. Moreover, all of them were under the control of Sigma70 promoter. The secondary structures of the sRNAs were derived using RNAfold and CentroidFold. IGR2780 contained a typical terminator, which is a stem-loop with a stretch of poly(U) sequence, whereas AS1974 and AS2779 contained only a typical I-shaped terminator. Notably, there was a canonical terminator in the middle of AS2779, suggesting that the RNA polymerase may stop the transcription at that position and generate a shorter form of AS2779.

Interaction Between sRNAs and Hfq

To understand the sRNA-Hfq interaction, in vitro RNA binding and electrophoretic mobility shift assay (EMSA) were performed using in vitro-transcribed P-aUTP-labeled RNA and purified recombinant *P. aeruginosa* Hfq protein. RsmY sRNA, which was previously shown to bind Hfq, was used as the positive control, whereas RsmY-reverse (the RNA with the reverse and complement sequence of RsmY) was the negative control in this experiment. It was shown that all sRNAs directly bound to Hfq protein with high specificity, except the rsmY-reverse sRNA (negative control).

Figure 2B:
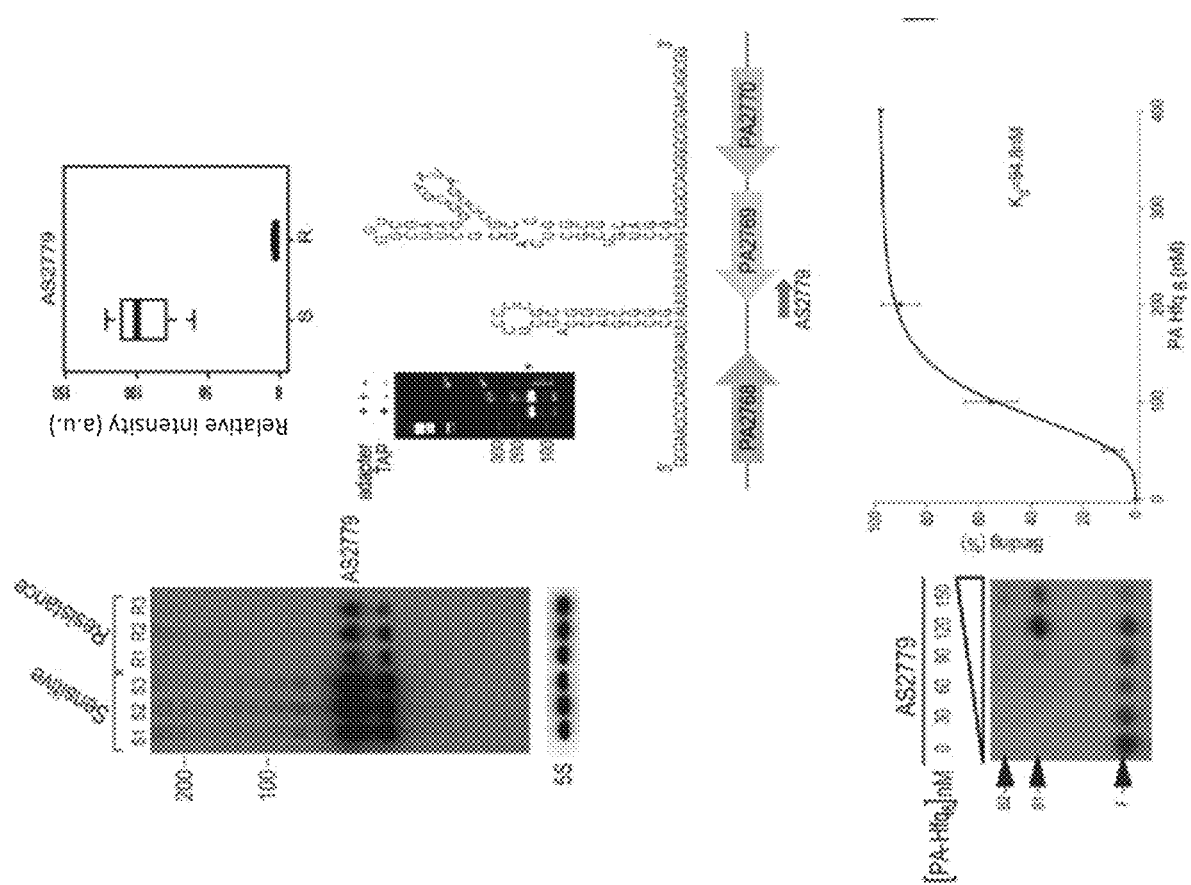
FIG. 2B shows the Northern blot analysis of 50 RACE, secondary structure prediction, and EMSA of AS2779 which has a sequence of SEQ ID NO: 4.
Figure 2C:
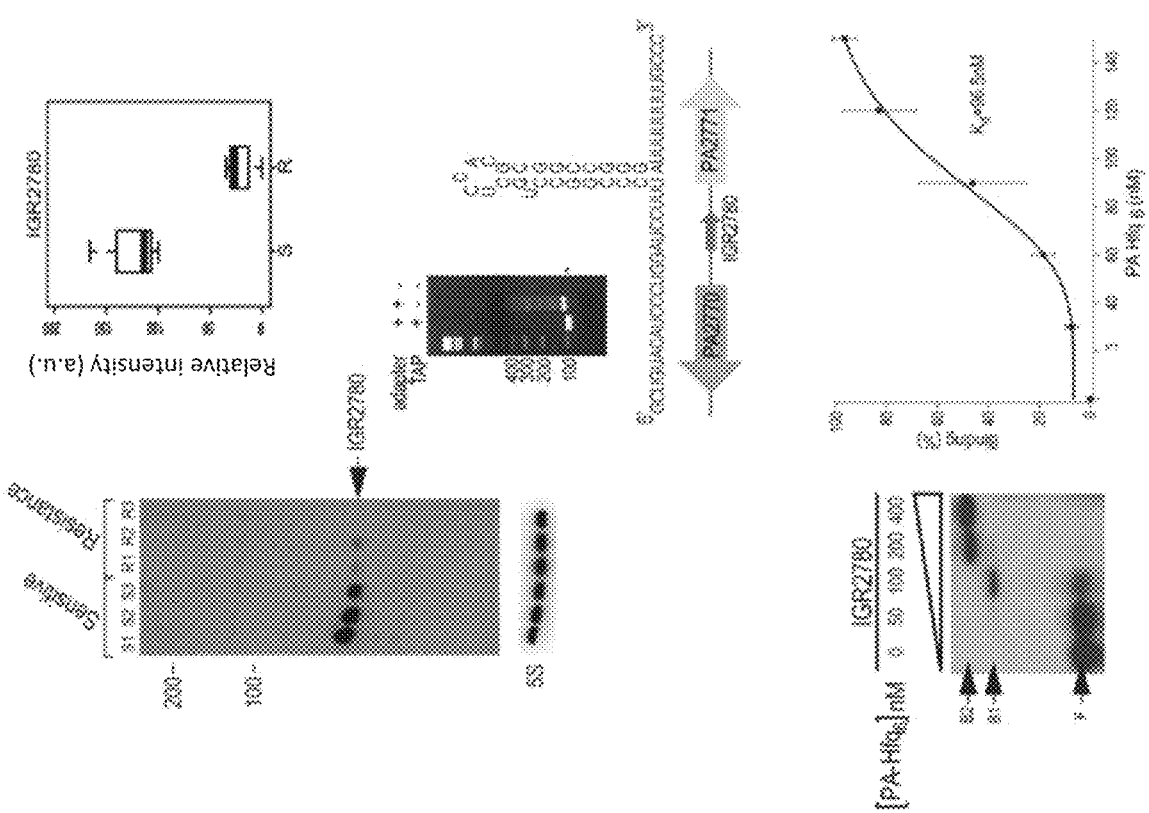
FIG. 2C shows the Northern blot analysis of 50 RACE, secondary structure prediction, and EMSA of IGR 2780 which has a sequence of SEQ ID NO: 3.

Moreover, the apparent dissociation constants (Kd) calculated from the binding isotherms of EMSA were less than 150 nM, indicating their high affinity to Hfq protein (FIG. 2A to FIG. 2C). Noteworthy, it was found that IGR2780 and AS2779 sRNAs possessed two cooperative binding sites to Hfq, which was similar to DsrA sRNA, the translational regulator of two global transcription regulators, H—NS and RpoS, in bacteria. These results suggested the versatility of these sRNAs to pair effectively with various target(s) at different extents in an Hfq-dependent manner.

Overexpression of AS1974 sRNA Induces Hypersusceptibility of the Resistance Strain As shown in FIG. 2A to FIG. 2C, three sRNAs were downregulated in drug-resistant strains compared with drug-susceptible strains. To find out if the sRNAs directly play a role in the intrinsic drug resistance of bacteria, each of the sRNAs was overexpressed in the resistance strains of *P. aeruginosa*, and MIC measurements were performed. Individual sequences of sRNAs were inserted into the modified pMMB66EH vector that was engineered for RNA expression and transformed into the resistance strains by electroporation. Empty vector was used as a control, and the strain of ATCC27853 was used as a reference for MIC measurement.

As shown in FIG. 1, overexpression of AS1974 in the transformed resistance strains displayed hypersusceptibility to aminoglycoside, cephalosporin, meropenem, and ertapenem, suggesting the functional roles of AS1974 sRNA in regulating the gene expression of these particular drug resistance pathways. To rule out the possibility of the non-specific effect from the sRNAs produced from the vector, we included AS1974-reverse as a negative control, which produced the same length but reverse and complement sequence of AS1974 in bacterial cell. As expected, the sRNA-reverse negative control showed no effect on the MIC (FIG. 1), indicating the specificity of AS1974 in regulating the drug resistance of *P. aeruginosa*.

Direct Control of MDR Gene Expression by AS1974 sRNA

Figure 3A:
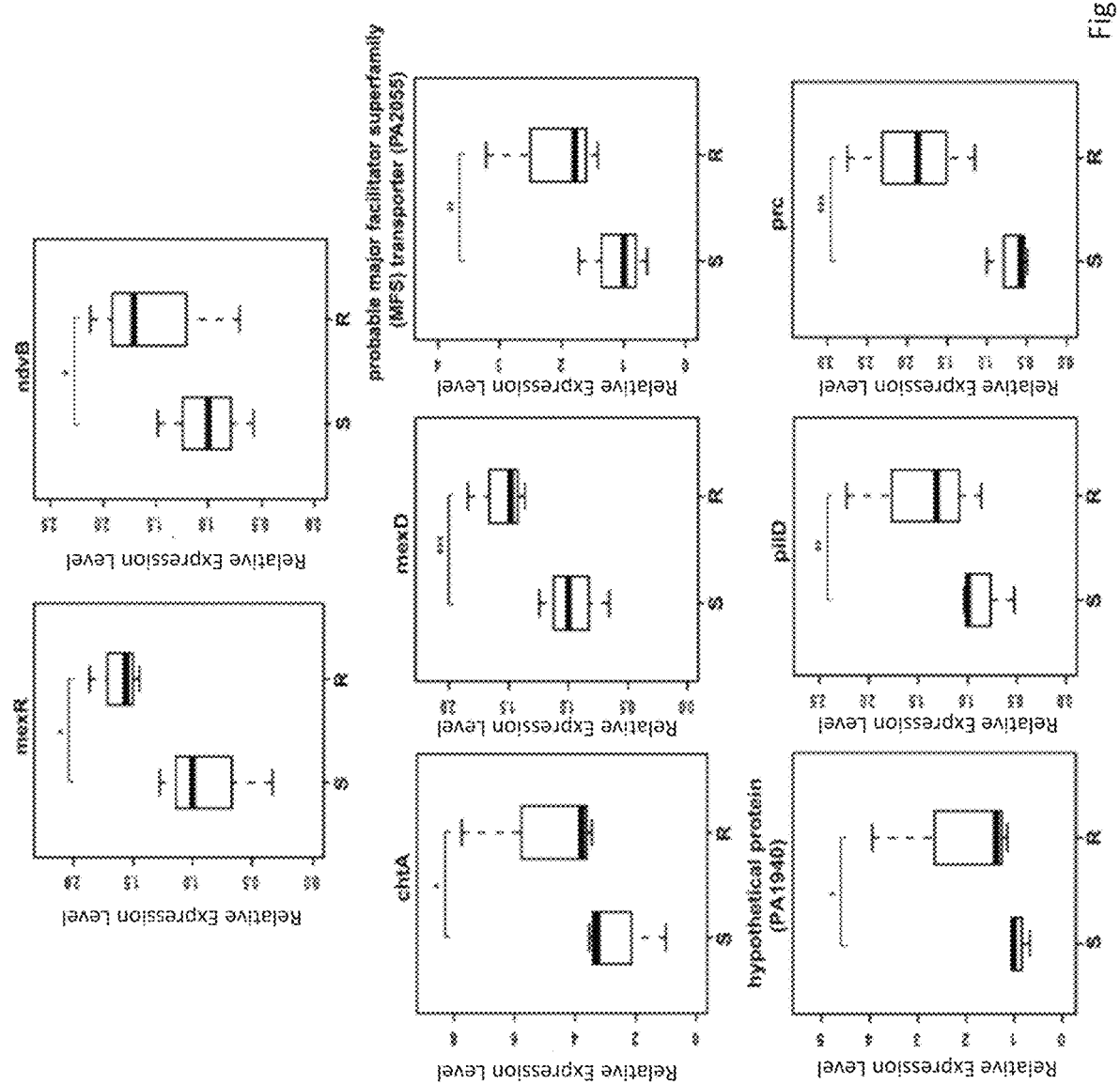
FIG. 3A shows the comparison of AS1974 target gene expression among antibiotic-resistant and -susceptible strains. The relative mRNA expressions of AS1974 target genes were measured using real-time PCR. The genes of three drug-resistant strains (R) were compared with three drug-susceptible strains (S) using boxplot, and the results were expressed as the means of at least 3 independent experiments.

One of the major functions of sRNAs is to suppress the target gene expression under particular conditions or in response to external stimuli. To find out the regulatory roles of AS1974 sRNAs in various drug resistance pathways, the inventors sequenced the transcriptomes of six strains, and they used newly developed program to correlate sRNA repertoires with transcriptomes. The inventors identified numerous target genes involved in drug resistance pathways, which were upregulated in all drug resistance strains, such as genes of membrane proteins (mexD, chtA, and prc), transporters (major facilitator superfamily), flagella (pilD), and antibiotic resistance (ndvB). To validate the transcriptome result, real-time qPCR experiments were performed to measure and compare the transcript levels of these genes in both drug-susceptible and drug-resistant strains. As shown in FIG. 3A, all the target genes were upregulated in the drug-resistant strains compared with the drug-susceptible strains, suggesting the role of AS1974 sRNA in post-transcriptional regulation of these transcripts.

Figure 3B:
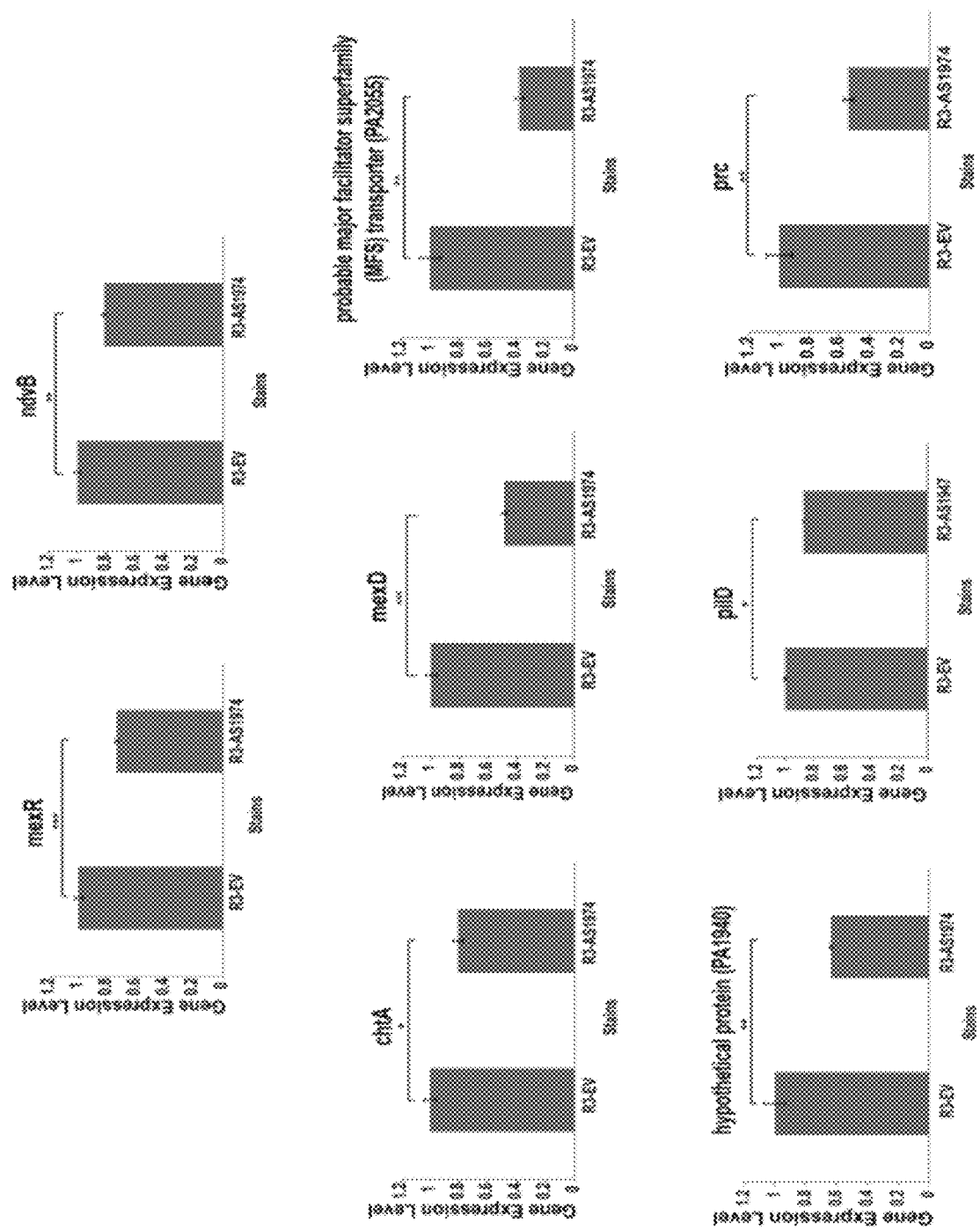
FIG. 3B shows the suppression of drug-resistant genes in AS1974-overexpressed transconjugants. The relative expressions of AS1974 target genes were measured in transconjugants that overexpressed AS1974 (R3-AS1974) and compared with control (transconjugants with empty vector [R3-EV]) using real-time PCR.

To further investigate if these drug-resistant genes were directly controlled by this sRNA, AS1974 was overexpressed in the resistance strain and their transcript levels were measured by qPCR. Empty vector was used as a negative control. As shown in FIG. 3B, all the target gene expressions were downregulated upon the overexpression of sRNA, indicating the functional roles of AS1974 in controlling the drug resistance of bacterial strains. Notably, ndvB is the biofilm-specific antibiotic-resistant gene. Overexpression of ndvB protein secretes the glucans that bind to the aminoglycoside, which prevents the molecules from entering the cell, and, therefore, the bacteria become resistant to aminoglycoside. These phenotypes were observed in the MIC study of transconjugant that overexpressed AS1974 sRNA (FIG. 1). The inventors also compared transcriptome profiles of AS1974-transformed and control strains, and found that less than 1% of the total transcripts was affected, indicating the off-target effect of AS1974 was minimal.

AS1974 sRNA Expression Is Regulated by Methylation in All MDR Strains

Figure 4A:
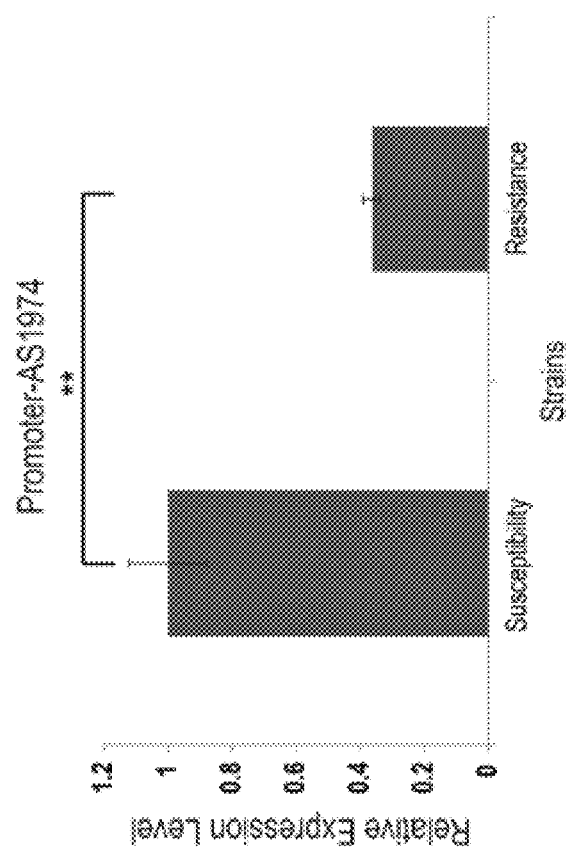
FIG. 4A is a plot obtained from ChIP-qPCR experiment in which the promoter of AS1974 was immunoprecipitated by the monoclonal antibody of transcription factor s70 from both resistant and susceptible strains and quantitated by qPCR experiments. The results were expressed as the means of at least 3 independent experiments. Data are presented as mean±SD, and comparisons were analyzed using unpaired t test (two tailed: *p<0.05, p<0.01, and *p<0.001).

AS1974 sRNA can control the drug resistance of clinical strains by mediating the expression of certain drug-resistant genes. To determine the regulation of AS1974 itself, the inventors set out to investigate the difference between the promoter region of drug-susceptible and drug-resistant strains. However, no mutation was found in the promoter regions of AS1974, suggesting that modification such as methylation may occur at the promoter region to regulate the sRNA expression. To investigate if there is any modification, the inventors first performed chromatin immunoprecipitation coupled to detection by real-time qPCR (ChIP-qPCR) experiments in both drug-susceptible and drug-resistant strains. As shown in FIG. 4A, stronger binding of RNA polymerase to the promoter region of AS1974 in the susceptible strain than in the MDR strain was observed, indicating that the occurrence of modification at the promoter region of AS1974 in the MDR strain, but not in the susceptible strain, reduced its affinity to the transcription factor. The inventors then performed the methylation analysis using Dpnl, the restriction enzyme that only cleaves the end of methylated adenine in the GATC recognition sequence and was generally used in epigenetic study in bacteria. However, no methylation was detected in both drug-susceptible and drug-resistant strains.

Figure 4B:
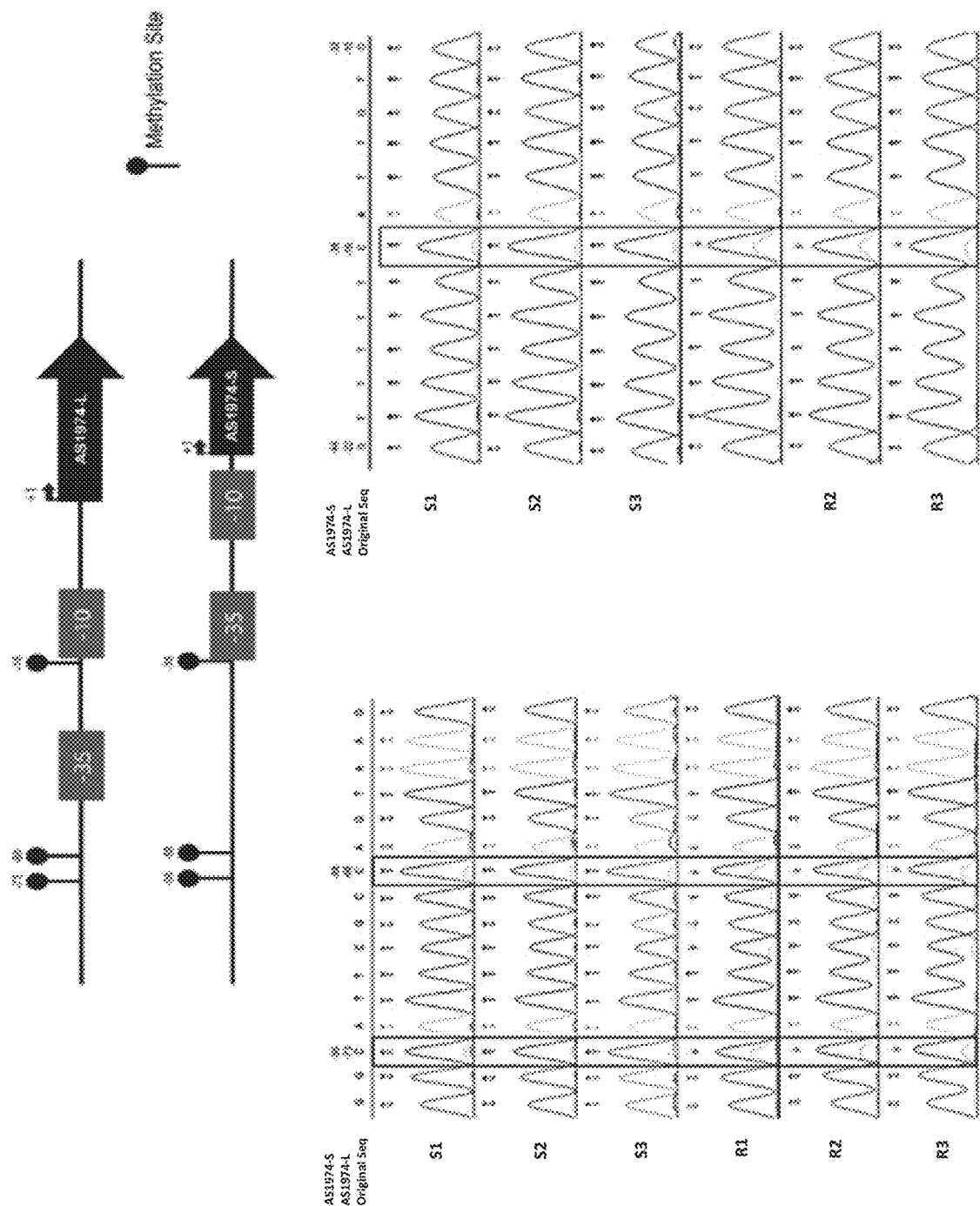
FIG. 4B demonstrates that the methylation of the promoter region of AS1974 was detected using bisulfite sequencing. Unmethylated cytosine residues were converted to uracil after bisulfite treatment and were detected as thymidine residues by Sanger sequencing. The methylation sites are depicted with the gene structure of AS1974. The transcription start site is shown with an arrow and numbering as +1 (upper). The sequencing chromatograms of six clinical strains at the promoter region of AS1974 are shown, and the methylation residues are highlighted (lower).

Finally, a bisulfite genomic sequencing analysis was performed to detect if there was any difference in the methylation pattern at the promoter region of AS1974 between drug-resistant and drug-susceptible strains. Since the bisulfite treatment of DNA converts cytosine residues to uracil but leaves 5-methylcytosine residues unaffected, sequencing the PCR products that amplified with specific primers can differentiate the single-nucleotide difference resulting from bisulfite conversion. As shown in FIG. 4B, the inventors found three methylation sites upstream of AS1974 in all resistant, but not susceptible, strains (long form at −16, −66, and −73 and short form at −38, −88, and −95), suggesting the methylation at these sites could inhibit the transcription of sRNA by blocking the binding site of RNA polymerase.

Figure 4C:
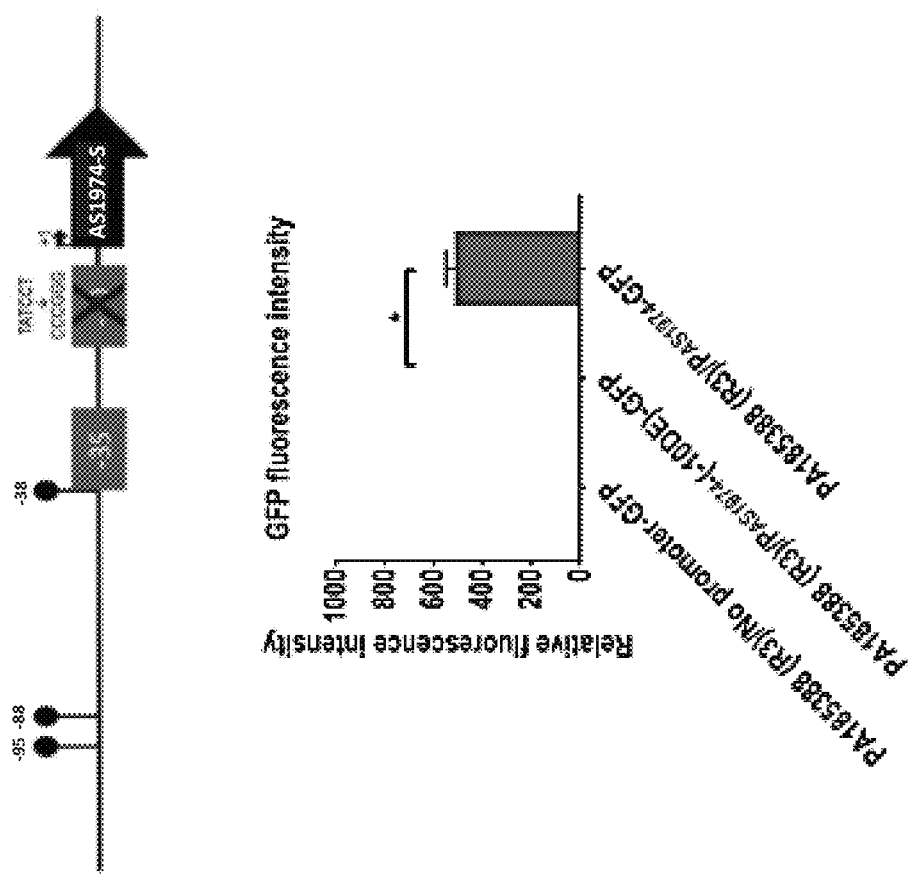
FIG. 4C illustrates a reporter system fused with the gene cassette of AS1974, including the promoter region to the GFP, and a plot showing the relative fluorescence intensity of the strains with or without mutation at the −10 position, particularly the Pribnow box sequence was mutated from TATCCT to CCCGGG.
Figure 4D:
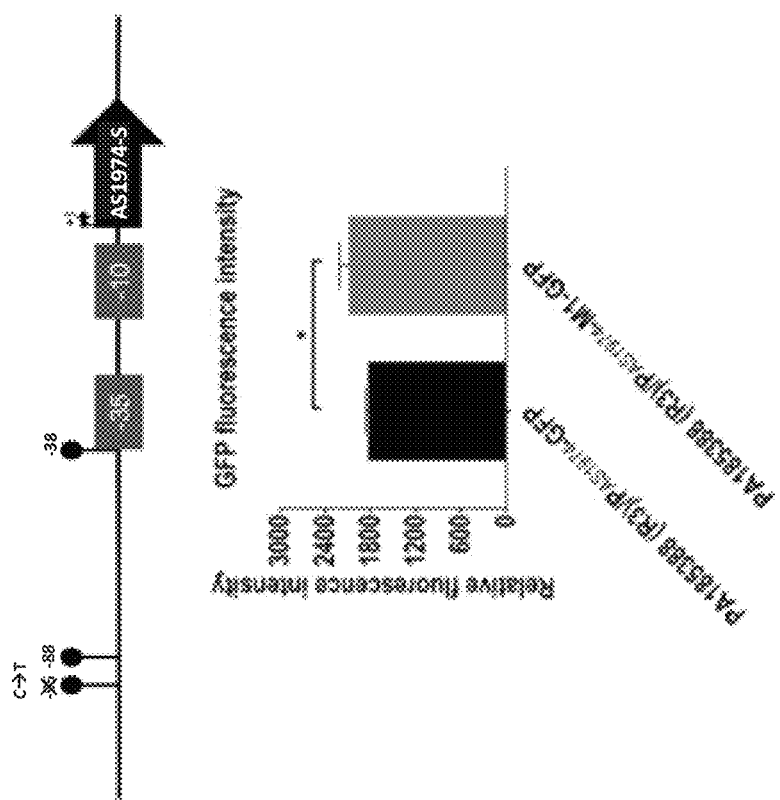
FIG. 4D illustrates a reporter system fused with the gene cassette of AS1974, including the promoter region to the GFP, and a plot showing the relative fluorescence intensity of the strains with or without C-T mutation at the first methylation M1 (−95).
Figure 4E:
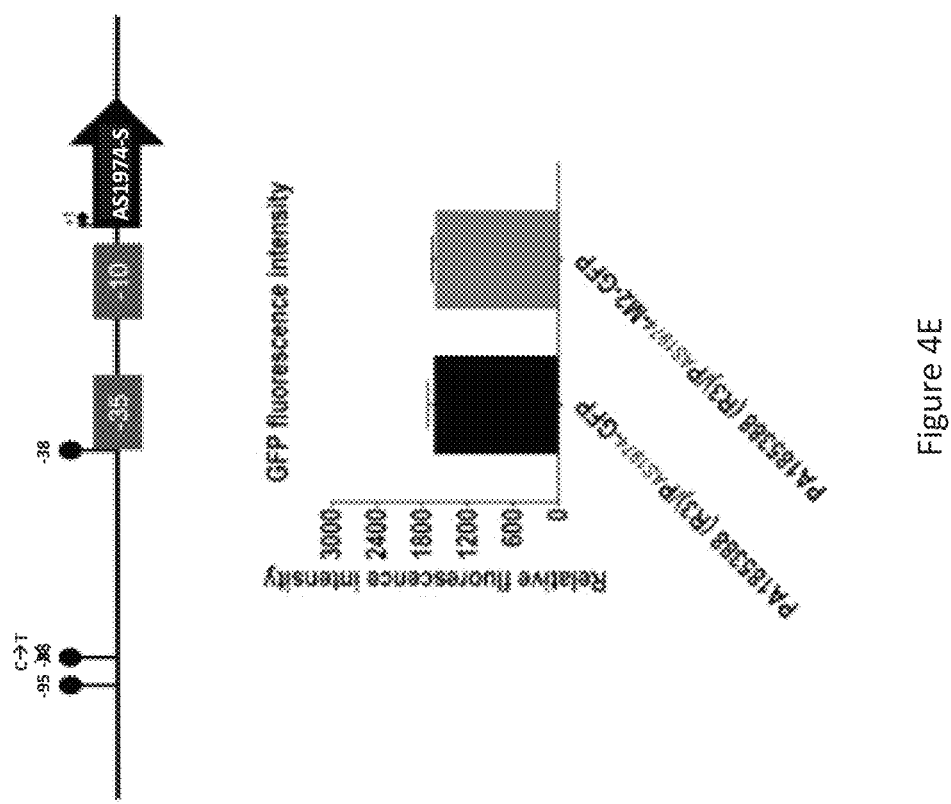
FIG. 4E illustrates a reporter system fused with the gene cassette of AS1974, including the promoter region to the GFP, and a plot showing the relative fluorescence intensity of the strains with or without C-T mutation at the second methylation M2 (−88).
Figure 4F:
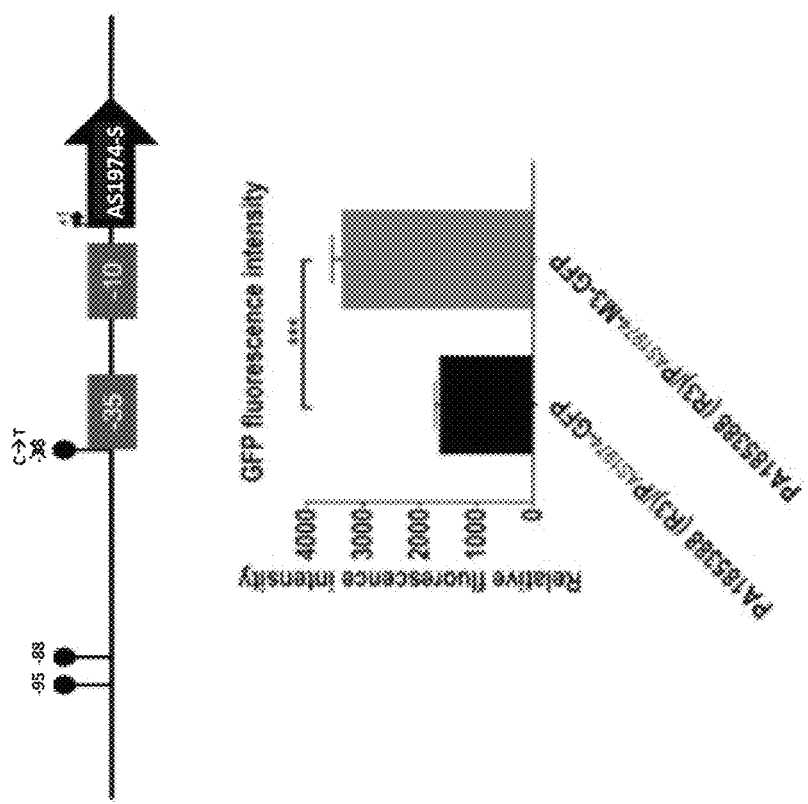
FIG. 4F illustrates a reporter system fused with the gene cassette of AS1974, including the promoter region to the GFP, and a plot showing the relative fluorescence intensity of the strains with or without C-T mutation at the third methylation M3 (−38).

As methylation at the promoter region can inhibit the binding of transcription factors and, in turn, control gene transcription, the inventors generated a reporter system that fused the gene cassette of AS1974, including the promoter region (P AS1974), to GFP, and the inventors investigated the influence of methylation on sRNA expression. Cassettes without promoter region and with Ptac promoter were used as negative and positive controls, respectively. After transforming the reporter systems into different strains, the inventors found that the fluorescence signal was higher in susceptible than resistant strains, indicating the transcription was suppressed in the resistant strains. Besides, that mutation at the −10 position of P AS1974 from TATCCT to CCCGGG sequences abolished the fluorescence signal of GFP further confirmed the position of the promoter region of AS1974 (FIG. 4C). Regarding the methylation sites, the fluorescence intensity of the strains carrying C-T point mutation at the first and third methylation sites (−95 and −38 of short form, respectively; FIGS. 4D and 4F), but not the second one (−88; FIG. 4E) was enhanced compared with the control, indicating the expression level of AS1974 was impaired by methylation in the resistant strains.

DISCUSSION

According to the experimental results, the inventors showed that the expressions of some sRNAs were significantly downregulated in the multidrug-resistant strains compared with those in the drug-susceptible strains. Moreover, overexpression of AS1974 sRNA transformed the bacteria from resistant strains to drug-sensitive strains. The identified sRNA is thus suitable candidate for eliminating the drug resistance of clinical isolates of *P. aeruginosa*. In other words, sRNA treatment in combination with old non-functional antibiotics (those that have been shown to be resistant and cannot be used for treatment) is possible approach to target the widely spreading multidrug resistance of bacterial infection in the world.

AS1974 sRNA was proven to downregulate the component of the multidrug efflux system, MexC-MexD-OprJ, which was the commonly found efflux pump in *P. aeruginosa*, and it provided resistance to aminoglycosides, chloramphenicol, and most b-lactams antibiotics except sulbenicillin and carbenicillin to the bacteria. Referring to FIG. 1, however, the AS1974-overexpressed strain still showed resistance to some antibiotics such as chloramphenicol. As the antibiotic resistance of bacteria is often attributed to multiple mechanisms, the observed resistance was indeed due to the contribution of other mechanisms. For example, the bacteria could secrete chloramphenicol acetyltransferase (CAT) to detoxify the chloramphenicol and become resistant to this particular antibiotic, which explains why AS1974-expressing strains were resistant to chloramphenicol and even the efflux system was affected.

Apart from the genes described above that target different types of molecules to protect the bacteria from antibiotics attack, other functional genes regulated by AS1974 were also found in other pathways, such as PA1940, pilD, and chtA. PA1940 is the putative catalase involved in oxidative stress, pilD functions in pilus biogenesis, and chtA is the TonB-dependent siderophore receptor that anchors on the outer membrane of the cell and controls iron acquisition. These genes have been shown to play roles in bacterial virulence, motility, and iron homeostasis. Intriguingly, chtA and prc are the major components of the cell surface signaling (CSS) regulatory system that controls extracytoplasmic function (ECF) sigma factors to regulate vital functions in the bacterial response to the environment in Gram-negative bacteria, and they were shown to play significant roles in the activation of the aerobactin-mediated CSS system in *P. putida*. Therefore, it is believed that AS1974 is capable of mediating the physiology of bacteria, in particular to the external stimuli, since sRNA provide immediate responses to the bacterial host to adapt to environmental changes for survival.

Material and Methods

Media and Growth Conditions

*P. aeruginosa* and *Escherichia coli* (*E. coli*) strains were grown aerobically at 37° C. in 100 mL Difco Nutrient Broth (Becton Dickinson) and Luria-Bertani (Affymetrix) medium separately with shaking at 250 rpm or on Difco Nutrient agar (Becton Dickinson) and Luria-Bertani (LB) agar (Affymetrix) plates. Ampicillin was used at the concentration of 100 mg/mL.

Bacterial Strains, Plasmids and Primers Bacterial strains, plasmids, and primers used in the experiments are listed in the following table.

TABLE 1

| *P. aeruginosa* strain | Description | Source or reference |
| --- | --- | --- |
| PA51530 (S1) | Clinical isolate, Sensitive | Laboratory collection |
| PA83365 (S2) | Clinical isolate, Sensitive | Laboratory collection |
| PA85710 (S3) | Clinical isolate, Sensitive | Laboratory collection |
| PA191712 (R1) | Clinical isolate, Multidrug resistance | Laboratory collection |
| PA194803 (R2) | Clinical isolate, Multidrug resistance | Laboratory collection |
| PA185388 (R3) | Clinical isolate, Mutidrug resistance | Laboratory collection |
| R3-AS1974 | R3 transformed with pMMB66EH-rrnBter-tet-AS1974 | This Study |
| R3-AS1974-Reverse | R3 transformed with pMMB66EH-rrnBter-tet-AS1974-Reverse | This Study |
| R3-IGR2780 | R3 transformed with pMMB66EH-rrnBter-tet-IGR2780 | This Study |
| R3-AS2779 | R3 transformed with pMMB66EH-rrnBter-tet-AS2779 | This Study |
| R3-Empty Vector | R3 transformed with pMMB66EH-rrnBter-tet | This Study |

| Plasmid(s) | Description | Source or reference |
| --- | --- | --- |
| pMMB66EH | Board-host-range expression vector; Ap$^r$ | ATCC |
| pMMB66EH-tet | Insert Transcription Unit of tet via Pst I site, Ap$^r$ Tet$^r$ | This Study |
| pMMB66EH-rrnBter-tet | Insert xba I-xho I-kpn I-rrnB terminator via Eco RI site, Ap$^r$ Tet$^r$ | This Study |
| pMMB66EH-rrnBter-tet-AS1974 | 0.128-kb xho I-kpn I AS1974 fragment cloned into the same site of pMMB66EH-rrnBter-tet | This Study |
| pMMB66EH-rrnBter-tet-AS1974-Reverse | 0.128-kb xho I-kpn I reverse complement of AS1974 fragment cloned into the same site of pMMB66EH-rrnBter-tet | This Study |
| pMMB66EH-rrnBter-tet-IGR2780 | 0.059-kb xho I-kpn I IGR2780 fragment cloned into the same site of pMMB66EH-rrnBter-tet | This Study |
| pMMB66EH-rrnBter-tet-AS2779 | 0.129-kb xho I-kpn I AS2779 fragment cloned into the same site of pMMB66EH-rrnBter-tet | This Study |

MIC Measurement

The MICs of 11 antibiotics, including penicillin G, cefotaxime, chloramphenicol, tetracycline, erythromycin, lincomycin, ciprofloxacin (Sigma, St. Louis, Mo., USA), levofloxacin (Daiichi Sankyo, Tokyo, Japan), gatifloxacin (Bristol-Myers Squibb, Moreton, UK), moxifloxacin (Bayer Healthcare Pharmaceuticals, Berlin, Germany), and linezolid (Pfizer, NJ, USA), were determined using the microbroth dilution method, according to the Clinical and Laboratory Standards Institute (CLSI).

Total RNA Preparation

Six *P. aeruginosa* strains, PA51530 (S1), PA83365 (S2), PA85710 (S3), PA191712 (R1), PA194803 (R2), and PA185388 (R3), were grown (100-mL culture) and harvested at OD600 1.5-1.7 (stationary phase). The cell pellet was lysed in 0.5 mg/mL lysozyme (Sigma-Aldrich) and extracted using 15 mL Trizol (Invitrogen). The total RNA was then treated with DNase I (New England Biolabs), and the rRNA was depleted using MICROBExpress Bacteria mRNA Enrichment Kit (Ambion), followed by Ribo-Zero rRNA Removal Kits (Gram-Negative Bacteria, Epicentre), according to the manufacturer's instructions. The quality and integrity of the extracted RNA was determined by Bioanalyzer (Agilent Technologies) and Qubit 2.0 Fluorometer (Life Technologies).

Purification of Recombinant Hfq Protein

The gene of hfq from *P. aeruginosa* was cloned into pET28a vector and transformed into BL21(DE3) pLysS *E. coli*. Overexpression of the recombinant protein was induced with 1 mM isopropyl b-D-1-thioga-lactopyranoside (IPTG) when OD600 reached 0.6 at 37° C. After 4-h induction, cells were harvested and lysed in lysis buffer (20 mM Tris, 150 mM NaCl, 0.5% Triton X-100, 0.4 mM phenylmethylsulfonyl fluoride (PMSF), and 2 mM 2-mercaptoethanol [b-ME] [pH 7.5]), followed by 5-min sonication on ice. The lysate was then centrifuged at 13,000 rpm at 4° C. for 45 min, and the supernatant was loaded onto column with TALON affinity resins (Clontech Laboratories). After extensive wash of the column, the protein was eluted and dialyzed overnight. The sample was then concentrated and the purity was analyzed by SDS-PAGE.

RNA Immunoprecipitation with Recombinant Hfq Protein and sRNA Sequencing 100 ng purified recombinant Hfq protein was immobilized on the 50 mL Gammabind G Sepharose beads (GE Healthcare) with anti-His 6 antibody, as described previously. Beads with antibody were used as a control. 10 mg total RNA extracted from the bacteria was added and incubated at 4° C. for 1 h with rotation. The beads were then washed extensively with RSB-100 containing 0.01% (v/v) NP-40. The immunoprecipitated RNA-protein complex was digested with 4 mL proteinase K at 45° C. for 1 h, and the RNA was extracted using acidic phenol: chloroform (5:1 [pH 4.5]; Ambion), followed by ethanol precipitation. The purified RNA then underwent rRNA depletion using Ribo-Zero rRNA Removal Kits (Gram-Negative Bacteria, Epicentre), according to the manufacturer's instructions, and the sequencing libraries were constructed and sequenced using Ion Torrent PGM sequencer, according to the protocol supplied by the company (Life Technologies).

Northern Blot Analysis

Six *P. aeru* strains, S1, S2, S3, R1, R2, and R3, were grown in 100 mL Nutrient broth with 250 rpm at 37° C. and harvested at OD600 1.5-1.7 (stationary phase). The cell pellet was lysed as described previously. Total RNA (10 mg) was denatured at 70° C. for 5 min in Gel Loading Buffer II (Ambion) and loaded onto 6% urea denaturing polyacrylamide gels. RNA was then transferred to Hybond-XL membrane (Amersham) and cross-linked under a UV light of 120 mJ/cm² for 2 min. DNA oligonucleotide probe specific for each sRNA was radioactively labeled with [γ–32P] ATP using T4 polynucleotide kinase (New England Biolabs) and further purified by Centri Spin column-20 (Princeton Separations). The membranes were incubated with probes at 42° C. overnight after prehybridization with UltraHyb buffer (Ambion), and then washed twice with 20 mL 0.2× sodium-sodium citrate (SSC) and 0.1% SDS for 10 min. The membranes were exposed to a phosphor screen overnight and visualized using a PhosphorImager (Typhoon TRIO, Amersham Biosciences).

The bands of the sRNAs are indicated and 5S was used as the loading control. The relative intensities of the bands were quantitated and analyzed by Image Processing and Analysis in Java software (ImageJ). The intensities of three drug-resistant strains (R) were compared with three drug-susceptible strains (S) using boxplot. The transcription start sites (TSSs) of each sRNA were determined using 50 RACE and the PCR results are shown. The band found in TAP and adaptor-treated RNA was cloned and sequenced to determine the TSSs. The secondary structure of each sRNA was predicted using the TSSs found in 50 RACE, and its orientation in the genome is depicted.

EMSA

The RNAs were in vitro transcribed and labeled with [α-32P] UTP using a MEGAScript kit (Ambion). The labeled sRNAs were further purified by 8M urea denaturing gel electrophoresis and precipitated with ethanol for subsequent experiments. To set up the EMSA reaction, 10,000 cpm labeled RNA was incubated with increasing concentrations (0-400 nM) of purified recombinant Hfq protein in binding buffer (50 mM Tris, 250 mM NH 4 CI [pH 7.5], 1× RNasin, and 10 mM tRNA) at 37° C. for 30 min. The samples were then mixed with 2 mL loading buffer (75% glycerol, 0.01% xylencyanol, and 0.01% bromphenol blue) and separated on 8% 1x Tris/Borate/EDTA (TBE) polyacrylamide gel. The image was analyzed by autoradiography. Signals of free and binding RNAs were quantified with ImageJ (NIH), and the binding percentages, which is equal to the intensity of all binding complex over the total intensity (including the free RNA and bound RNA), were calculated. The curves were fitted with the Hill equation using the Igor Pro program (WaveMetrics), using default settings to estimate the $K_d$ values of each binding isotherm.

Construction of pMMB66EH-rrnBter-tet

Plasmid pMMB66EH (ATCC 37620) was purchased from ATCC. To construct pMMB66EH-rrnBter-tet, the transcription unit (TU) of tetracycline resistance gene was cloned from the pACYC184 vector, using the primers of Tet-Pstl-F (5'-CGACTGCAGAGATTTCAGTGCAATTTATCTCT-3', SEQ ID NO: 5) and Tet-Pstl-R (5'-GATCTGCAGTTCACAGTTCTCCGCAAGAATTG-3', SEQ ID NO: 6), and inserted into the Pstl site. The clone carrying pMMB66EH-rrnB-tet with the desired direction was selected and validated by Sanger sequencing (Beijing Genomics Institute [BGI]).

Construction of pMMB66EH-rrnBter-tet-sRNA

The sRNA sequences were amplified from P. aeruginosa genomic DNA by PCR and cloned into the Xhol and Kpnl sites of pMMB66EH-rrnBter-tet to generate pMMB66EH-rrnBter-tet-sRNA constructs. The clone carrying pMMB66EH-rrnB-tet-sRNAs was selected and validated by Sanger sequencing (BGI). The recombinant plasmids were then transformed into P. aeruginosa by electroporation for further studies.

Electroporation

The sRNAs were amplified from genomic DNA and cloned into the in-house RNA expression vector (pMMB66EH-rrnBter-tet). The vector carrying sRNA was then transformed into P. aeruginosa MDR strains by electroporation under the conditions of 25 microfarad (uF), 2.5 kV, and 200U. The transformed cells were plated on the nutrient agar plates with tetracycline at the concentrations of 16, 32, 64, and 128 mg/mL and incubated at 37° C. overnight.

Real-Time qPCR

Six P. aeruginosa strains, S1, S2, S3, R1, R2, and R3, were grown at 37° C. overnight in nutrient broth with shaking at 250 rpm and harvested at stationary phase (OD600=1.5-1.7). The growth conditions for R3-EV and R3-A51974 transformed strains were the same as described above, except for using tetracycline at 128 mg/mL. Total RNA extracted from P. aeruginosa was reverse transcribed using SuperScript III First-Strand Synthesis SuperMix for qRT-PCR (Invitrogen). Real-time qPCR was performed on an ABI Fast 7500 real-time PCR machine (Applied Biosystems). All real-time PCR assays were run in a total reaction of 10 mL consisting of 1×SYBR Green Master Mix (Applied Biosystems) and 200 nM primers. Cycling conditions were 2 min at 50° C., then 10 min at 95° C., followed by 40 cycles of amplification (15 s at 95° C. and 1 min at 60° C.). Melting curves were determined by an auto-dissociation program. The house-keeping gene rpsL was used for normalization. The comparative CT method (2×DDCT) was used to calculate the relative expression level of the target genes. The results were expressed as the means of at least 3 independent experiments. Data are presented as mean±SD, and comparisons were analyzed using unpaired t test (two tailed: *$p<0.05$, $p<0.01$, and *$p<0.001$).

RACE

5' RACE was carried out using FirstChoice RML-RACE kit (Ambion) with a modified protocol. Total RNA was treated with Tobacco acid pyrophosphatase (TAP). 5' RACE RNA adaptor was ligated to the TAP-treated RNA, followed by reverse transcription using random primers. Controls without TAP treatment and/or without adding adaptor were included. PCR was performed using a forward primer specific to the 5' RACE adaptor and reverse primers specific to target sRNAs. The amplified PCR fragment was subsequently cloned into pGEM-T easy vector (Promega) and then sequenced. TSSs of sRNAs were identified by sequencing the junction between the adaptor and the sRNAs.

Methylation Analysis by Bisulfite Sequencing

The bisulfite sequencing of genomic DNA (gDNA) was performed using EpiTect Plus DNA Bisulfite Kit (QIAGEN), according to the manufacturer's protocol. Briefly, 0.5 mg gDNA of six clinical strains was added individually to the PCR tubes containing DNA Protect Buffer and Bisulfite Mix and placed into the thermal cycler for bisulfite conversion. The converted DNAs were then purified and subjected to PCR amplification with the primers located at −150 and 50 nt of AS1974 sRNA for Sanger sequencing. The methylated cytosine residues that could not be converted to uracil showed the cytosine in sequencing results.

ChIP-qPCR

P. aeruginosa strains PA51530 (S1) and PA185388 (R3) were grown in 50-mL cultures to OD600=1.7 (stationary phase) and treated with formaldehyde (final concentration of 1%) for 20 min at room temperature. The cross-linking reactions were quenched by glycine at the final concentration of 250 mM. The cells were harvested by centrifugation, washed twice with ice-cold Tris-buffered saline (20 mM Tris-HCl [pH 7.5] and 150 mM NaCl), and stored at −80° C. The pellets were re-suspended in immunoprecipitation buffer (50 mM HEPES-KOH [pH 7.5], 150 mM NaCl, 1 mM EDTA, 1% Triton X-100, 0.1% sodium deoxycholate, and Roche complete protease inhibitor cocktail) and sonicated by bioruptor (Bioruptor Plus, Diagenode) to shear DNA to an average size of 0.25-1 kb. Cell debris was then removed by centrifugation, and the supernatant with an equal amount of protein concentration was used for the immunoprecipitation experiment. Gammabind G Sepharose (GE Healthcare), which was previously equilibrated and bound with RNA polymerase sigma 70 monoclonal antibody (GeneTex), was incubated with the supernatant overnight at 4° C. on a rotating wheel. The beads were then collected and washed twice with immunoprecipitation (IP) buffer, once with IP buffer plus 500 mM NaCl, once with wash buffer III (10 mM Tris-HCl [pH 8.0], 250 mM LiCl, 1 mM EDTA, 0.5% Non-idet-P40, and 0.5% sodium deoxycholate), and once with Tris-EDTA buffer (pH 7.5). Immunoprecipitated complexes were eluted from the beads by treatment with 100 mL elution buffer (50 mM Tris-HCl [pH7.5], 10 mM EDTA, and 1% SDS) at 65° C. for 30 min. Samples were then treated with RNase A for 2 h at 37° C., and the cross-links were reversed by overnight incubation at 65° C. in 0.5× elution buffer with proteinase K. The DNA after proteinase digestion was further purified using a DNA purification Kit (GE Healthcare) and used for qRT-PCR experiments, as described above.

PAS1974-GFP Reporter Construction

PAS1974-GFP reporter plasmids were constructed by fusing the promoter region of sRNAs AS1974, including 130 bp(AS1974-S)/112 bp(AS1974-L) upstream of the start codon, to GFP and cloned into pMMB66EH vector. Antibiotic marker tet-R from pACYC184 was also cloned into pMMB66EH in order to perform selection after transformation to the bacterial strains. pMMB66EH with the gfp gene but without a promoter was used as a negative control plasmid, whereas pMMB66EH with the gfp gene controlled by the Ptac promoter was used as a positive control plasmid. Three methylation sites (M1, M2, and M3) were individually mutated from C to T in the PAS1974-GFP plasmid. For promoter region, position −10 of the promoter region was mutated from TATCCT to CCCGGG. The plasmids were subsequently transformed into the P. aeruginosa drug-resistant strain R3 (PA185388) and drug-sensitive strain S2 (PA83365).

PAS1974-GFP Reporter Assays

Reporter strains were cultured in nutrient broth (NB) supplemented with 32 mg/mL (for S2) and 128 mg/mL (for R3) tetracycline at 37° C. Cultures were diluted 3-fold in NB and added to 96-well clear-bottom assay plates for measurement. NB only was used as blanks. After overnight growth, fluorescence signal was measured on a multi-plate reader with the excitation wavelength at 405 nm and the emission wavelength at 510 nm. Relative GFP fluorescence intensity was calculated as follows: the fluorescence intensity/OD600 nm at the test time point.

The invention claimed is:

1. A method of inhibiting growth of a multi drug-resistant (MDR) bacterium comprising steps of:
   a) delivering a polynucleotide comprising a sequence of SEQ ID NO: 1 or SEQ ID NO: 2 to the MDR bacterium;
   b) transforming the MDR bacterium into a drug-sensitive bacterium, and
   c) contacting the bacterium with an effective amount of an antibiotic; wherein the bacterium is *Pseudomonas aeruginosa*.

2. The method of claim 1, wherein the polynucleotide is encapsulated in a bacteriophage or a nanoparticle to be delivered to *P. aeruginosa*.

3. The method of claim 1, wherein the antibiotic inhibits growth of a gram-negative bacterium.

4. The method of claim 1, wherein the antibiotic is selected from the group consisting of an aminoglycoside antibiotic, a cephalosporin antibiotic, a beta-lactam antibiotic, a fluoroquinolone antibiotic, or a combination thereof.

5. The method of claim 1, wherein the antibiotic is selected from the group consisting of amikacin, gentamicin, tobramycin, ceftibuten, cefepime, ceftazidime, cefriaxone, ceforaxmine, cefoperazone, sulbactam, imipenem, meropenem, ertapenem, peperacillin, tazobactam, moxifloxacin, pefloxacin, norfloxacin, fleroxacin, tigecycline, chloramphenicol, or a combination thereof.

6. The method of claim 1, wherein the step c) is performed simultaneously or after the step a).

7. The method of claim 1, wherein the MDR bacterium has a drug-resistance against at least two antibiotics before being treated or introduced with the polynucleotide in step a).

8. A method of treating a subject suffering from an infection caused by a multi drug-resistant (MDR) bacterium, wherein the MDR bacterium is *Pseudomonas aeruginosa* and the method comprises:
   i) delivering a polynucleotide comprising SEQ ID NO: 1 or SEQ ID NO: 2 to a tissue infected by the MDR bacterium or to a MDR bacterium in the subject;
   ii) transforming a MDR bacterium into a drug-sensitive bacterium, and
   iii) administering an effective amount of an antibiotic to the subject; wherein the MDR bacterium possess resistance to the antibiotic prior to step i).

9. The method of claim 8, wherein the polynucleotide is encapsulated in a bacteriophage or a nanoparticle.

10. The method of claim 8, wherein the antibiotic is selected from the group consisting of an aminoglycoside antibiotic, a cephalosporin antibiotic, a beta-lactam antibiotic, a fluoroquinolone antibiotic, or a combination thereof.

11. The method of claim 8, wherein the antibiotic is selected from the group consisting of amikacin, gentamicin, tobramycin, ceftibuten, cefepime, ceftazidime, cefriaxone, ceforaxmine, cefoperazone, sulbactam, imipenem, meropenem, ertapenem, peperacillin, tazobactam, moxifloxacin, pefloxacin, norfloxacin, fleroxacin, tigecycline, chloramphenicol, or a combination thereof.

* * * * *